(12) United States Patent
Heydenreich et al.

(10) Patent No.: US 6,710,211 B1
(45) Date of Patent: Mar. 23, 2004

(54) METHOD FOR THE PRODUCTION OF BISPHENOL-A

(75) Inventors: Frieder Heydenreich, Düsseldorf (DE); Michael Prein, Brasschaat (BE); Michael Bödiger, League City, TX (US); Rainer Neumann, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/129,944

(22) PCT Filed: Nov. 3, 2000

(86) PCT No.: PCT/EP00/10827

§ 371 (c)(1), (2), (4) Date: Aug. 26, 2002

(87) PCT Pub. No.: WO01/36358

PCT Pub. Date: May 25, 2001

(30) Foreign Application Priority Data

Nov. 15, 1999 (DE) .......................................... 199 54 786

(51) Int. Cl.$^7$ .............................................. C07C 37/60

(52) U.S. Cl. ....................................................... 568/724
(58) Field of Search ......................................... 568/724

(56) References Cited

U.S. PATENT DOCUMENTS

| | | | |
|---|---|---|---|
| 5,414,151 A | 5/1995 | Pressman et al. | 568/727 |
| 5,545,764 A | 8/1996 | Berg et al. | 568/724 |
| 5,723,689 A | 3/1998 | Pressman et al. | 568/724 |
| 5,785,823 A | 7/1998 | Meurer et al. | 203/71 |

FOREIGN PATENT DOCUMENTS

| | | |
|---|---|---|
| EP | 0 522 700 | 1/1997 |
| EP | 0 829 464 | 3/1998 |
| EP | 0 718 267 | 12/1998 |
| JP | 05117189 | * 5/1993 |

* cited by examiner

Primary Examiner—Taofiq Solola
(74) Attorney, Agent, or Firm—Joseph C. Gil; John E. Mrozinski, Jr.; Jennifer R. Seng

(57) ABSTRACT

2,2-bis(4-hydroxyphenyl)propane (BPA) is produced by reacting acetone and phenol in the presence of cross-linked sulfonated polystyrene resins and then separating the BPA off from the reaction solution.

3 Claims, 1 Drawing Sheet

METHOD FOR THE PRODUCTION OF BISPHENOL-A

This application is a 371 of PCT/EP00/10827 filed Nov. 3, 2000.

FIELD OF THE INVENTION

The invention relates to a process for the efficient production of high-purity bisphenols.

BACKGROUND OF THE INVENTION

Bisphenols are important raw materials for the production of polymers such as epoxy resins or, in particular, polycarbonates. High standards of purity are required of the bisphenols used for this purpose, so that for economic, large-scale production processes, in addition to the attainment of high conversion rates and selectivities in the reaction, the working-up steps are also of particular importance.

In the principally known processes, bisphenols are produced by condensing carbonyl compounds with aromatic alcohols in the presence of acid catalysts. A process for the industrially important production of 2,2-bis(4-hydroxyphenyl)propane (BPA) is the reaction of acetone and phenol in the presence of cross-linked sulfonated polystyrene resins (ion-exchange resins). Here a phenol/acetone ratio of at least 5:1 is established. To attain higher selectivities, cocatalysts are used; these are either homogeneously dissolved in the reactants or fixed to the ion-exchange resin by covalent or ionic bonds.

The object is to separate off the secondary products formed in the above process for producing BPA from the BPA by suitable procedures and to completely remove excess phenol from the product. In addition, the side streams formed during these procedures should be economically recycled in the overall process.

A mean of achieving these objects which has been described in the literature is the isolation of BPA-phenol adduct crystals from the reaction solution by suspension cystallisation, with or without prior distillation for the removal of water, acetone and phenol (EP-A 829 464, EP-A 522 700 and EP-A 671 377). Here, the highly phenolic mother liquor obtained during the filtration of the adduct crystals, optionally after the insertion of a rearrangement reaction, is returned to the front of the reaction unit and replenished with fresh phenol and acetone. In order to achieve higher purities, the suspension crystallisation may optionally be carried out repeatedly in series. A disadvantage of this process is the necessity of using expensive apparatus for the crystallisation and for the solid-liquid separation. Moreover, the coating of the surfaces of this apparatus with BPA or BPA-phenol adducts presents a problem during the suspension crystallisation and necessitates a regular cleaning of the surfaces by melting the deposits (EP-A 718 267).

In order to, circumvent these problems, processes which dispense with an adduct crystallisation and consequently with the production of a circulating flow of mother liquor have been proposed in EP-A 758 637. Here BPA is carried out by working up the flow of reactants in a cascade of purification steps involving distillation, the flow of reactants being purified without the generation of return flows of acetone, water, phenol and secondary products. Disadvantages of this process are the heat stress on the product owing to the high temperatures during the distillation, the high energy costs of the distillation cascade and the high loss of raw materials as a result of dispensing with rearrangement and return.

EP-A 785 181 describes the working-up of the reaction solution, likewise dispensing with an adduct crystallisation, by a combination of vacuum distillation for the removal of acetone, water, phenol and possibly secondary components and subsequent melt crystallisation. In this procedure as well, there are inevitable losses of raw materials as a result of dispensing with a return of the flows of BPA-containing secondary products formed during the purification.

SUMMARY OF THE INVENTION

The process according to the invention for the working-up of high-purity BPA avoids the disadvantages described above by carrying out the adduct crystallisation from the flow of reactants in the form of a layer crystallisation.

DETAILED DESCRIPTION OF THE INVENTION

Figure 1:
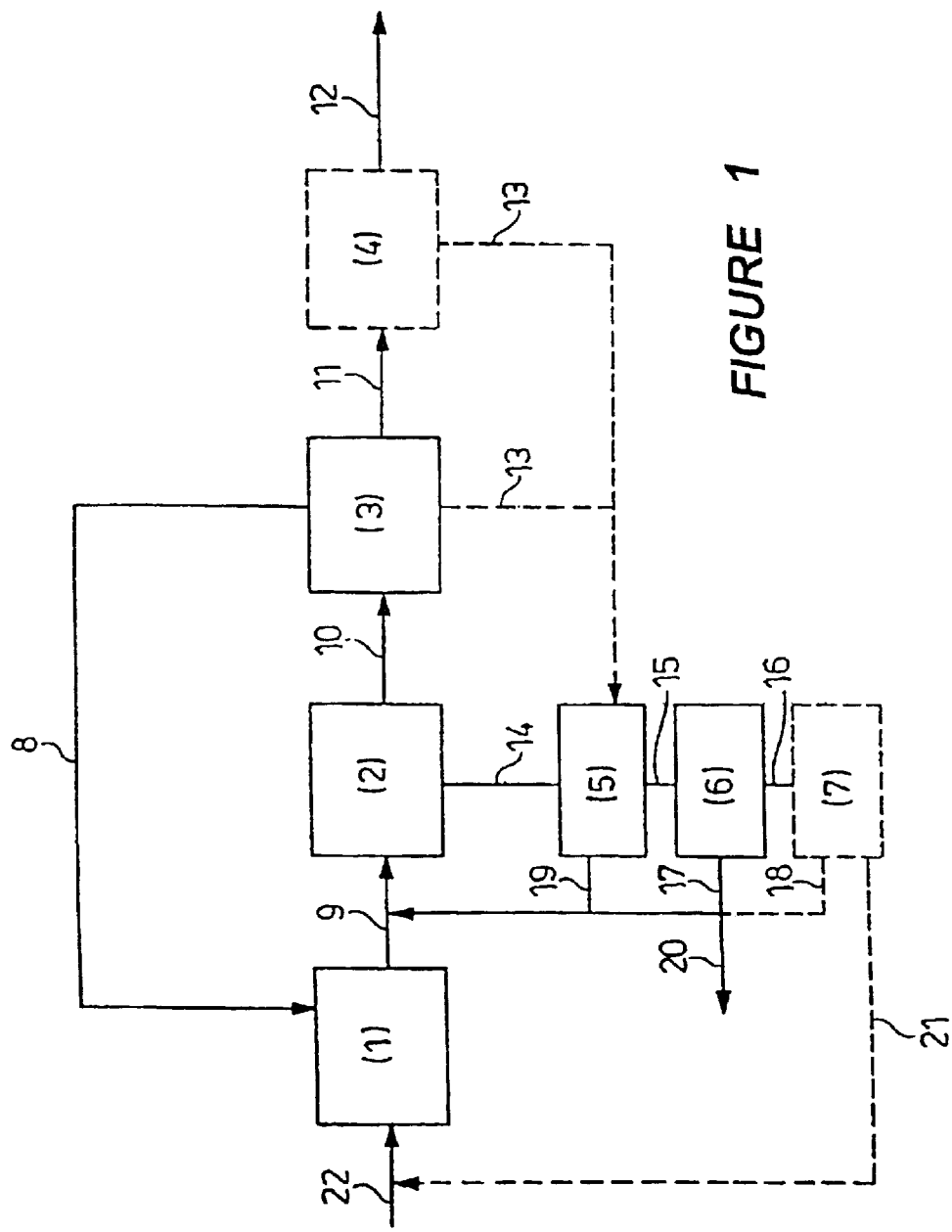
FIG. 1 depicts a reaction unit for carrying out the process of the instant invention.

The invention provides a process for producing 2,2-bis (4-hydroxyphenyl)propane (BPA) by reacting acetone and phenol in the presence of cross-linked sulfonated polystyrene resins (ion-exchange resins), characterised in that, subsequent to the reaction unit, BPA is separated off from the reaction solution a) by a primary crystallisation in the form of a layer crystallisation operated continuously or batchwise, b) and purified by distillation or crystallisation, c) and the circulating flow of material from the layer crystallisation, separated from BPA and enriched with secondary products, with the insertion of a rearrangement reaction and of a distillation for the removal of water, acetone and optionally phenol, is returned to the front or the rear of the reactor.

This procedure makes it possible to dispense with the use of a suspension crystallisation and with the use of filters and/or centrifuges for the mechanical solid-liquid separation.

The process according to the invention is illustrated in more detail in the diagram of the process in FIG. 1.

(1) represents a reaction unit, in which phenol, acetone and optionally secondary products of the BPA production returned via the circulating flow of mother liquor, with a phenol/acetone ratio of at least 5:1, preferably at least 10:1, at temperatures of 40° C. to 110° C., preferably 45° C. to 70° C., are fed into an ion-exchange catalyst system, consisting of a sulfonated cross-linked polystyrene.

Either the ion-exchange catalyst system is modified with a covalently or ionically bonded mercapto compound, or a suitable mercapto compound is added homogeneously to the reaction solution and circulated.

The reaction unit is for example and preferably a layered bed or fluid bed through which substances flow upwards or downwards, or a column designed for a reactive distillation.

The flow of reactants (reaction solution) issuing from the reaction unit (1) contains unreacted phenol and acetone, as well as water, BPA and the secondary products typically formed during the reaction, such as o,p-BPA, indanes, chromanes, and more highly condensed reaction products having three or more than three aromatic nuclei.

This flow of reactants is passed to a crystallisation unit (2), in which the crystallisation is carried out as a layer crystallisation on cooled surfaces in a melt crystallisation apparatus operated continuously or batchwise at temperatures of 30° C. to 110° C., preferably 35° C. to 80° C. The crystallisation can be carried out statically or in the form of a falling-film crystallisation.

When crystal growth has finished, the crystals formed are isolated by letting out the liquid mother liquor. Optionally, a further purification of the crystals is subsequently carried out, for example and preferably by passage through a temperature gradient by sweating. Finally, the crystals are liquefied by elevating the temperature above the melting point and are then let out into a collecting tank for further processing. The mixture obtained here contains p,p-BPA (50–70%), phenol (30–50%) and secondary components (0.1–10%).

This mixture is passed to a unit for the removal of phenol (3), in which phenol is removed by processes known in principle, for example and preferably by distillation or desorption, to concentrations of <0.5%, preferably <0.1%.

Optionally, the p,p-BPA thus obtained is then purified in a second purification unit (4), for example and preferably either by a one-step or multistep distillation or again by layer crystallisation, to a purity of at least 99.5%, preferably at least 99.85%.

The flow of mother liquor obtained in the crystallisation unit (2) is preferably passed through a rearrangement reactor (5), which is filled with acidic ion-exchange material and operated at temperatures of 50° C. to 10° C., preferably 60° C. to 80° C. The rearrangement of a portion of the secondary products contained in the return flow (o,p-BPA, higher condensates) into p,p-BPA is thereby brought about and the product yield is thus increased.

Phenol and/or acetone are optionally introduced into the rearrangement reactor (5), as required.

The flow of material obtained at the outlet of the rearrangement reactor (5) is led away in order to be worked up by multistep distillation, water and acetone being separated off in a distillation unit (6) and phenol optionally being separated off in distillation unit (7).

The phenol obtained here is returned to the reaction unit (1) and used for the production of BPA.

The flow of bottom products in the distillation unit (7), which is enriched with BPA and isomers, is passed to the front of the crystallisation unit (2).

In an alternative variant of the process, the separation of phenol in the distillation unit (7) is dispensed with and the flow of mother liquor, after separation of water and acetone in the distillation unit (6), is returned directly to the reaction unit (1). A portion of the flow of mother liquor may optionally be withdrawn from the process.

In the diagram of the process in FIG. 1, in addition:
(8) is a return duct for phenol
(9) to (11) are ducts for the flow of reactants
(12) is a unit for removing the product
(13) and (13') are ducts for secondary products
(14) to (19) are ducts for the flow of mother liquor
(20) is a unit for removal
(21) is a return duct for phenol
(22) is a feed unit for phenol and acetone Through the process according to the invention, high-quality BPA is obtained economically with a minimisation of return flows, energy input and losses of materials. The use of rotary filters and centrifuges for the separation of adduct crystals in the suspension crystallisation of BPA can be dispensed with in the production process. Consequently, the operation of technologically expensive processing apparatus requiring considerable maintenance is avoided and the availability of the plant is increased. Owing to its high purity and favourable colour index, the BPA produced in this way is particularly suitable for use as raw material for polymers such as polycarbonates or epoxy resins.

The following Examples serve to illustrate the invention. The invention is not limited to the Examples. Percentages given below denote percentages by weight.

EXAMPLES

Example 1

A continuously operating test apparatus as shown in FIG. 1, with separation of phenol (7) is used. The following conditions and concentrations are established in equilibrium in the individual processing steps:

Reaction unit (1): Filled with sulfonated polystyrene resin, moistened with phenol (Lewatit SC 104, Bayer AG, modified with 5% cysteamine), inlet temperature:

65° C., flow rate: 0.21 reaction solutions catalyst * h

Concentration at the inlet: phenol 96%, acetone 4.0%

Concentration at the outlet: phenol 84.5%, acetone 0.25%, water 1.45%, p,p-BPA 12.8%, secondary components 1.0%.

Layer crystallisation (2): Operated as static layer crystallisation with the following individual steps: crystallisation (63° C. to 36° C.), letting out the mother liquor, sweating (36° C. to 61° C.), melting of the product (61° C. to 110° C.).

Concentration at the inlet: phenol 70.2%, acetone 0.2%, water 1.4%, p,p-BPA 21.2%, secondary components 7.0%.

Concentration at the outlet, product flow: phenol 42.2%, acetone <0.1%, water <0.1%, p,p-BPA 56.4%, secondary components 1.4%.

Concentration at the outlet, flow of mother liquor: phenol 85.0%, acetone 0.3%, water 2.2%, p,p-BPA 2.5%, secondary components 10.0%.

Removal of phenol (3): Operated as a one-step desorption unit with nitrogen, temperature at the bottom 190° C.

Concentration at the inlet: phenol 42.2%, p,p-BPA 56.4%, secondary components 1.4%.

Concentration at the outlet: phenol <0.1%, p,p-BPA 97.6%, secondary components 2.4%.

Final purification (4): Operated as static layer crystallisation with the following individual steps: crystallisation, letting out the mother liquor, sweating, melting of the product.

Concentration at the inlet: phenol <0.1%, p,p-BPA 97.6%, secondary components 2.4%.

Concentration at the outlet: p,p-BPA 99.84%, secondary components 0.16%.

Rearrangement reaction (5): Filled with sulfonated polystyrene resin, moistened with phenol (Lewatit SC 104, Bayer AG, modified with 5% cysteamine), inlet temperature: 80° C., flow rate: 0.21 reaction solution/1 catalyst * h Removal of water/acetone (6): Packed column operated at 150 mbar, 140° C. temperature at the bottom, separation of water and acetone in the product flow to <0.1%

Separation of phenol (7): Packed column operated at 100 mbar, overhead temperature 120° C.; the flow of phenol returned to the front of the reaction unit showed a purity of 99.9%.

The quantity of BPA resin passed out of the return flow to the front of the crystallisation unit was 8% of the returned quantity.

What is claimed is:

1. A process for the production of p,p-bisphenol A (BPA) comprising the steps of
   a) reacting acetone and phenol in the presence of a cross-linked sulfonated polystyrene resin,
   b) crystallizing the reactants in a crystallization unit wherein, the crystallization is layer crystallization, the crystallization is carried out continuously or batchwise, and a mixture containing p,p-BPA, phenol and secondary components is obtained,
   c) purifying the mixture by distillation or desorption, wherein p,p-BPA is obtained,
   d) optionally performing a second purification of the p,p-BPA by distillation or crystallization,
   e) circulating the mixture through a rearrangement reactor, wherein the reactor contains an acidic ion-exchange material, and
   f) distilling water, acetone or phenol off the mixture.

2. The process according to claim 1, wherein the cross-linked sulfonated polystyrene resin is modified with a covalently or ionically bonded mercapto compound.

3. The process according to claim 2, wherein the tonically bonded mercapto compound is 2-mercaptoethylamine (cysteamine).

* * * * *